(12) United States Patent
Modarresi et al.

(10) Patent No.: US 9,464,014 B2
(45) Date of Patent: Oct. 11, 2016

(54) PROCESS FOR THE PREPARATION OF METHANOL IN PARALLEL REACTORS

(71) Applicant: Haldor Topsøe A/S, Kgs. Lyngby (DK)

(72) Inventors: Hassan Modarresi, Lyngby (DK); Christian Wix, Nærum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/892,124

(22) PCT Filed: May 15, 2014

(86) PCT No.: PCT/EP2014/059962
§ 371 (c)(1),
(2) Date: Nov. 18, 2015

(87) PCT Pub. No.: WO2014/206635
PCT Pub. Date: Dec. 31, 2014

(65) Prior Publication Data
US 2016/0107961 A1    Apr. 21, 2016

(30) Foreign Application Priority Data
Jun. 27, 2013 (EP) ..................... 13174010

(51) Int. Cl.
| C07C 27/00 | (2006.01) |
| C07C 29/152 | (2006.01) |
| B01J 8/04 | (2006.01) |
| B01J 8/02 | (2006.01) |
| B01J 19/18 | (2006.01) |

(52) U.S. Cl.
CPC ............ *C07C 29/152* (2013.01); *B01J 8/0292* (2013.01); *B01J 8/0453* (2013.01); *B01J 19/1856* (2013.01); *B01J 2208/00274* (2013.01); *B01J 2208/027* (2013.01)

(58) Field of Classification Search
CPC . C07C 29/152; C07C 31/04; C07C 29/1516; B01J 8/067; B01J 2208/00274; B01J 2219/0004
USPC ........................................................ 518/708
See application file for complete search history.

(56) References Cited

U.S. PATENT DOCUMENTS

| 4,766,154 A * | 8/1988 | Bonnell .............. C07C 29/1516 518/700 |
| 5,827,901 A | 10/1998 | Konig et al. |
| 2011/0065966 A1 | 3/2011 | Mueller et al. |
| 2011/0178188 A1 | 7/2011 | Kopetsch et al. |

FOREIGN PATENT DOCUMENTS

| DE | 40 04 862 A1 | 8/1991 |
| JP | S 51131813 A | 11/1976 |
| WO | WO 2011/101081 A1 | 8/2011 |

OTHER PUBLICATIONS

Ullman's Encyclopedia of Industrial Chemistry, 6th Edition, chapter "Methanol", see subchapter 5.2, "Synthesis" pp. 1-27 (1998).

* cited by examiner

*Primary Examiner* — Jafar Parsa
(74) *Attorney, Agent, or Firm* — Blank Rome LLP

(57) ABSTRACT

In a process for the preparation of methanolin parallel reactors, comprising the steps of (a) reacting carbon oxides and hydrogen in the presence of a methanol catalyst in a first methanol reactor to obtain a first methanol-containing effluent, (b) introducing and reacting unconverted synthesis gas in a second methanol reactor in the presence of a methanol catalyst to obtain a second methanol-containing effluent, the first methanol reactor and the second methanol reactor being connected in parallel, (c) combining the first and second effluent, and (d) cooling and separating the combined and cooled effluent into a methanol-containing liquid phase and unconverted synthesis gas, the methanol catalyst in the first methanol reactor is indirectly cooled by boiling water and the methanol catalyst in the second methanol reactor is either directly or indirectly cooled by the unconverted synthesis gas prior to conversion into the second effluent.

8 Claims, 2 Drawing Sheets

PROCESS FOR THE PREPARATION OF METHANOL IN PARALLEL REACTORS

Figure 1:
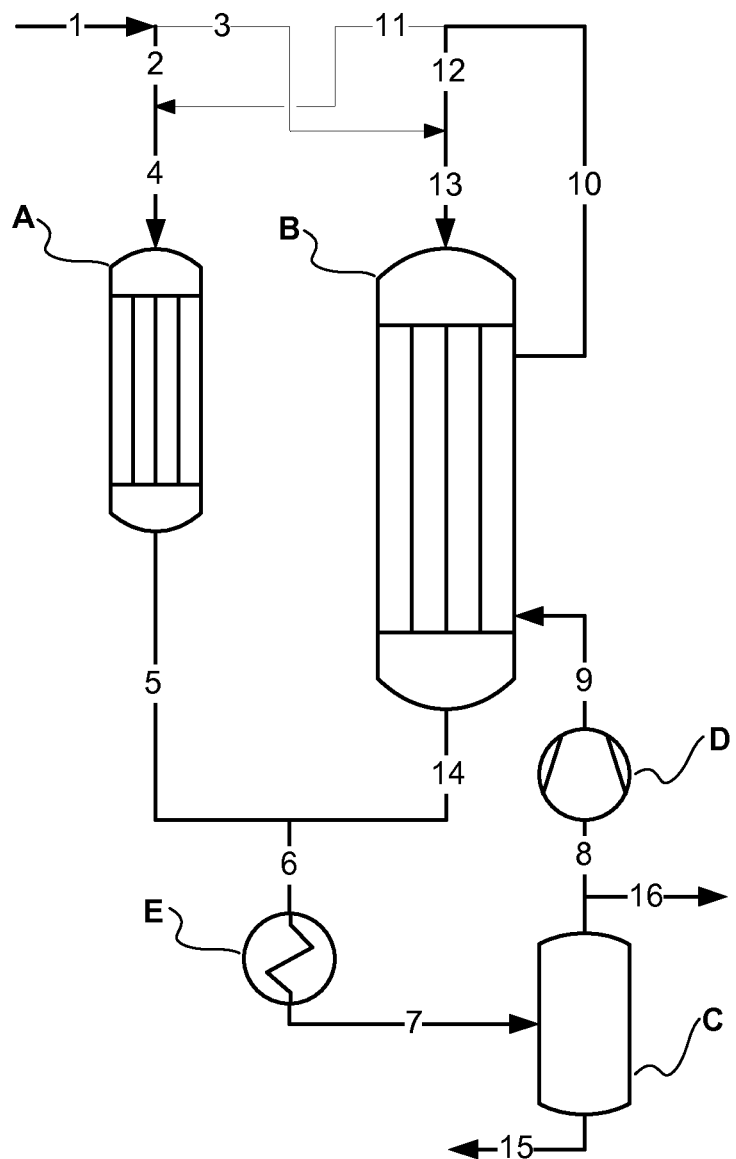

The present invention relates to a novel process for the preparation of methanol in parallel reactors.

Methods for the production of methanol by catalytic conversion of synthesis gas containing hydrogen and carbon oxides have been known for a long time to persons skilled in the art. A single-stage method for the production of methanol is for example described in Ullman's Encyclopedia of Industrial Chemistry, $6^{th}$ edition (1998) chapter "Methanol", sub-chapter 5.2 "Synthesis".

U.S. Pat. No. 5,827,901 describes a process for producing methanol from a synthesis gas containing hydrogen and carbon oxides, where the synthesis gas is passed through a first synthesis reactor provided with a catalyst and then through a second synthesis reactor, also provided with a catalyst which is cooled with synthesis gas. The two reactors are connected in series.

Another process for producing methanol from a synthesis gas containing hydrogen and carbon oxides is described in US 2011/0178188. The synthesis gas is passed through a first, water-cooled reactor in which a part of the carbon oxides is catalytically converted to methanol. The resulting mixture of synthesis gas and methanol vapour is led to a second, gas-cooled reactor, connected in series to the first reactor, in which a further part of the carbon oxides is converted to methanol. After separating methanol from the synthesis gas, the gas is recirculated to the first reactor.

A process for methanol production, very similar to the above and again with the reactors connected in series, is described in US 2011/0065966. In order to achieve a maximum methanol yield even with an aged catalyst, a partial stream of the recirculated synthesis gas is guided past the first reactor and introduced directly into the second reactor.

WO 2011/101081 A1 describes the preparation of methanol by means of a catalytic process with a plurality of serial synthesis stages, in which the severity of the reaction conditions, measured on the basis of the reaction temperature and/or the concentration of carbon monoxide in the synthesis gas, decreases from the first to the last reaction stage in the flow direction. The first reaction stage uses a first catalyst with low activity but high long-term stability, while the last reaction stage uses a second catalyst with high activity but low long-term stability.

DE 40 04 862 C2 describes a method for methanol synthesis using at least two methanol synthesis reactors, said reactors both (or all) being multi-bed reactors. These reactors, which can be arranged in series or in parallel, are all fed with the same feed flows and patterns, whereas in the present invention the first reactor is fed with either fresh synthesis gas or a mixture of fresh synthesis gas and recycle gas. The purpose of the invention described in the DE publication is to establish improved reaction conditions, especially including optimization of the reactors leading to savings in reactor volumes.

Finally, JP published application no. S51-131813 describes a process for methanol production comprising the steps of first introducing a starting material gas comprising carbon oxides and hydrogen into a non-circulating reactor to partially react said gas and then introducing unreacted gas contained in the outlet gas from the non-circulating reactor into a circulating reactor to react said outlet gas. It appears from the drawings that the connection between the non-circulating reactor and the circulating reactor is serial.

In a standard methanol synthesis loop, a boiling-water reactor (BWR) is used to convert the gas mixture of fresh synthesis gas from a reformer/gasifier unit (called makeup gas in the following) and recycle gas, i.e. unconverted synthesis gas.

Since BWRs are expensive, many efforts have been made to minimize the size of the reactor in the methanol plant or even to replace it with a cheaper reactor, such as a gas-cooled reactor (GCR).

The basic idea of using a GCR is to utilize the methanol synthesis heat to directly heat up the cold recycle gas. A GCR is quite similar to a BWR as regards the mechanical structure, yet it can be cheaper than the BWR, which is due to equalized operating pressures inside the tubes and the shell.

In the novel process according to the present invention a GCR or a multi-bed quench reactor is employed together with a BWR, the two reactors being used in parallel in the methanol synthesis process. This arrangement enables CO concentration flexibility in order to control the maximum temperature in each of the parallel reactors. The recycle gas is less strong (i.e. having a relatively low percentage of CO) than the makeup gas.

Yet another aspect of the invention is that it can enable the plant operators to operate the BWR at a fixed steam pressure from the start-of-run (SOR) to the end-of-run (EOR) of the plant by adjusting the strength of the BWR feed gas. For instance, the BWR would receive feed gas lean in carbon monoxide by adding more carbon monoxide lean recycle gas to the carbon monoxide rich makeup gas at SOR condition, when the catalyst is fresh and highly active. At the EOR, when the catalyst is aged/deactivated, stronger feed gas can be introduced to the BWR by restricting or cutting the recycle gas to it. These two operational scenarios can assure a constant steam pressure/temperature ratio generated by the BWR.

The process according to the invention can be used in new methanol production plants, but it is also usable for revamping of existing plants in order to increase the capacity of such plants.

More specifically, the present invention relates to a novel process for the preparation of methanol, said process comprising the steps of a) reacting carbon oxides and hydrogen in the presence of a methanol catalyst in a first methanol reactor to obtain a first methanol-containing effluent;

b) introducing and reacting unconverted synthesis gas in a second methanol reactor in the presence of a methanol catalyst to obtain a second methanol-containing effluent, the first methanol reactor and the second methanol reactor being connected in parallel;

c) combining the first and second effluent, and d) cooling and separating the combined and cooled effluent into a methanol-containing liquid phase and unconverted synthesis gas.

In this process, the methanol catalyst in the first methanol reactor is indirectly cooled by boiling water and the methanol catalyst in the second methanol reactor is indirectly cooled by the unconverted synthesis gas prior to conversion into the second effluent.

The characteristic feature of connecting the reactors in parallel is that both reactors are fed with a feed gas that does not contain methanol. As a consequence, the reactors do not need to operate at lower temperatures, i.e. below 230° C., as it is the case with reactors connected in series, e.g. described in US 2011/0065966. Further, unlike the methanol production process described in US 2011/0065966, where different types of methanol catalysts must be used in the two reactors because of the temperature difference (high temperature in the BWR and lower temperature in the GCR), a single type of methanol catalyst can be used in the two reactors in the process according to the invention.

The two reactors can receive different fractions of the makeup gas and the recycle gas flows.

In the process according to the invention, the carbon oxides and hydrogen in the BWR are provided by a mixture of fresh synthesis gas and a part of the unconverted synthesis gas. Furthermore, the gaseous phase is contacted with the methanol catalyst after having directly or indirectly cooled the methanol catalyst in the second reactor.

The carbon oxides and hydrogen in the BWR are provided by a mixture of fresh synthesis gas and the gaseous phase from step d) of the above process. Furthermore, the carbon oxides and hydrogen in the GCR are provided by a mixture of the gaseous phase from step d) of the above process and the fresh synthesis gas.

Figure 2:
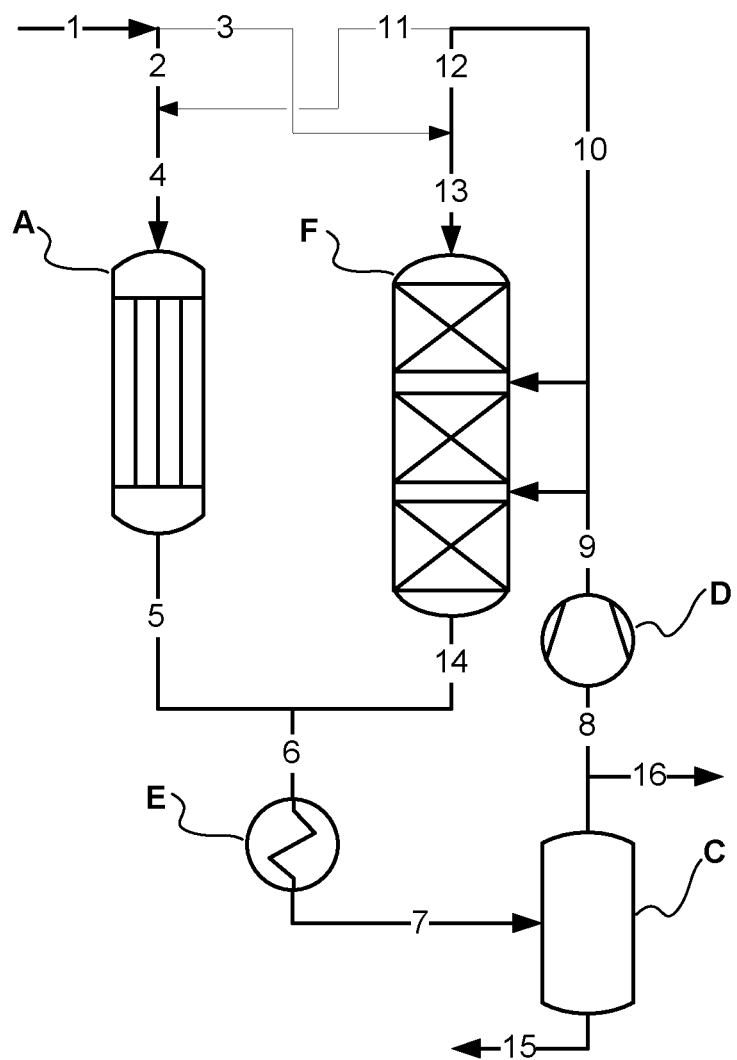

The process according to the invention is described in further detail with reference to the drawings, where FIG. 1 is a preferred process layout with a GCR, and FIG. 2 is an alternative process layout, in which the GCR has been replaced by a multistage packed-bed reactor.

According to the process layout shown in FIG. 1, the makeup gas (1), i.e. the synthesis gas, is split into two streams (2) and (3). One stream (2) is mixed with a part of the pre-heated recycle gas (11). The resulting mixed gas (4) is fed to the BWR (A).

The other part of the makeup gas (3) is mixed with another part of the pre-heated recycle gas (12). The resulting mixed gas (13) is fed to the GCR (B).

The effluents from the two reactors, i.e. (5) and (14), are mixed, and the resulting stream (6) is cooled down in the cooler (E). The cooled product stream (7) is separated into the raw methanol product (15) and an unconverted gas stream in the gas/liquid separator (C).

The unconverted gas stream from the separator (C) is divided into the purge stream (16) and a cold recycle gas stream (8). The purpose of purging a small fraction of the recycle gas is to prevent accumulating the inert gases in the synthesis loop.

The cold recycle gas stream (8) is pressurized by passage through the gas compressor (D). The pressurized gas (9) is used for removing the heat of reaction, which is generated in the GCR (B). This is done by indirect cooling, and the heated recycle gas (10) is split up into two streams (11) and (12) and fed to the reactors (A) and (B), respectively.

An alternative to the process layout described above is shown in FIG. 2. In this alternative layout the GCR is replaced by a multistage packed-bed reactor (F). In this case the heat of reaction is removed by direct injection of a part of the cold recycle gas (9) between the beds of the reactor (F). The remaining part of the cold recycle gas (10) can be divided and fed to either or both of the reactors (A) and (F). A pre-heating of stream (10) may be necessary. The layout in FIG. 2 may resemble that of DE 40 04 862 C2, but the present layout contains only two reactors (non-identical), whereas that of DE 40 04 862 C2 can contain more than two reactors, which are all of the same type.

The invention is illustrated further in the following examples. More specifically, the process as conducted in the process layout of FIG. 1 is illustrated and compared in two examples.

EXAMPLE 1

In this example, the makeup gas (which is rich in carbon monoxide) is mixed with a part of the recycle gas (which is lean in carbon monoxide) and fed to the boiling water reactor (BWR). Thereby the concentration of carbon monoxide in the BWR feed gas drops from 28 mole % to 19.8 mole %. The GCR only receives the recycle gas with a carbon monoxide concentration of 11.2 mole %.

This scenario of operation can be applied during SOR of the plant when the catalyst is fresh and highly active.

EXAMPLE 2

In this example, a part of the makeup gas is also fed to the GCR in order to increase the carbon monoxide concentration in the GCR feed gas stream to 21.1 mole %, and consequently to decrease the carbon monoxide concentration in the BWR feed gas stream to 15.5 mole %.

Alternatively, the recycle gas stream to the BWR can be restricted or even cut in order to increase the carbon monoxide concentration in the BWR feed gas and further dilute the GCR feed gas. In this case, this operational scenario may be used at the EOR of the plant.

By adjusting the split ratio of the recycle gas between the BWR and the GCR it is possible to control the maximum temperature of the catalytic bed by adjusting the carbon monoxide concentration in the feed gas for both reactors.

In both examples, the operating pressure of the synthesis loop is about 90 barg. In the following table, the process conditions in the two examples are compared.

Comparison of two alternative processes for parallel BWR and GCR

| Stream | T (° C.) | Flow × 10³ (Nm³/h) |  | $H_2$ | CO | $CO_2$ | $H_2O$ | $CH_3OH$ | Inert Gases |
|---|---|---|---|---|---|---|---|---|---|
| Ex. 1 | | | | | | | | | |
| 1 | 220 | 211 | mole % | 66.5 | 28.0 | 3.0 | 0.50 | 0.00 | 2.00 |
| 2 | 220 | 211 | mole % | 66.5 | 28.0 | 3.0 | 0.50 | 0.00 | 2.00 |
| 3 | 220 | 0 | mole % | 66.5 | 28.0 | 3.0 | 0.50 | 0.00 | 2.00 |
| 4 | 222 | 413 | mole % | 67.1 | 19.8 | 4.6 | 0.25 | 0.25 | 8.00 |
| 5 | 260 | 326 | mole % | 58.1 | 12.0 | 5.6 | 0.62 | 13.5 | 10.1 |
| 6 | 208 | 479 | mole % | 58.6 | 9.72 | 5.8 | 0.90 | 12.6 | 12.4 |
| 7 | 40 | 479 | mole % | 58.6 | 9.72 | 5.8 | 0.90 | 12.6 | 12.4 |
| 8 | 40 | 386 | mole % | 67.7 | 11.2 | 6.3 | 0.00 | 0.50 | 14.3 |
| 9 | 45 | 386 | mole % | 67.7 | 11.2 | 6.3 | 0.00 | 0.50 | 14.3 |
| 10 | 225 | 386 | mole % | 67.7 | 11.2 | 6.3 | 0.00 | 0.50 | 14.3 |
| 11 | 225 | 202 | mole % | 67.7 | 11.2 | 6.3 | 0.00 | 0.50 | 14.3 |
| 12 | 225 | 184 | mole % | 67.7 | 11.2 | 6.3 | 0.00 | 0.50 | 14.3 |
| 13 | 225 | 184 | mole % | 67.7 | 11.2 | 6.3 | 0.00 | 0.50 | 14.3 |
| 14 | 123 | 153 | mole % | 59.7 | 5.00 | 6.0 | 1.60 | 10.7 | 17.0 |

-continued

| | | | Comparison of two alternative processes for parallel BWR and GCR | | | | | | |
|---|---|---|---|---|---|---|---|---|---|
| Stream | T (° C.) | Flow × 10³ (Nm³/h) | | H₂ | CO | CO₂ | H₂O | CH₃OH | Inert Gases |
| 15† | 40 | 2,170* | wt % | 0.10 | 0.30 | 3.2 | 3.90 | 92.0 | 0.30 |
| 16 | 40 | 284 | mole % | 67.7 | 11.2 | 6.3 | 0.01 | 0.54 | 14.3 |
| Ex. 2 | | | | | | | | | |
| 1 | 220 | 211 | mole % | 66.5 | 28.0 | 3.0 | 0.50 | 0.00 | 2.0 |
| 2 | 220 | 148 | mole % | 66.5 | 28.0 | 3.0 | 0.50 | 0.00 | 2.0 |
| 3 | 220 | 63 | mole % | 66.5 | 28.0 | 3.0 | 0.50 | 0.00 | 2.0 |
| 4 | 224 | 497 | mole % | 67.7 | 15.5 | 5.6 | 0.20 | 0.40 | 10.6 |
| 5 | 258 | 408 | mole % | 60.0 | 8.70 | 6.2 | 0.90 | 11.3 | 13.0 |
| 6 | 207 | 483 | mole % | 59.2 | 8.90 | 6.1 | 0.80 | 12.6 | 12.4 |
| 7 | 40 | 483 | mole % | 59.2 | 8.90 | 6.1 | 0.80 | 12.6 | 12.4 |
| 8 | 40 | 390 | mole % | 68.2 | 10.3 | 6.7 | 0.00 | 0.50 | 14.3 |
| 9 | 45 | 390 | mole % | 68.2 | 10.3 | 6.7 | 0.00 | 0.50 | 14.3 |
| 10 | 225 | 390 | mole % | 68.2 | 10.3 | 6.7 | 0.00 | 0.50 | 14.3 |
| 11 | 225 | 350 | mole % | 68.2 | 10.3 | 6.7 | 0.00 | 0.50 | 14.3 |
| 12 | 225 | 40 | mole % | 68.2 | 10.3 | 6.7 | 0.00 | 0.50 | 14.3 |
| 13 | 222 | 104 | mole % | 67.2 | 21.1 | 4.5 | 0.30 | 0.20 | 6.70 |
| 14 | 89 | 75 | mole % | 54.7 | 10.5 | 5.9 | 0.60 | 19.0 | 9.30 |
| 15 | 40 | 2,170* | wt % | 0.10 | 0.30 | 3.4 | 3.70 | 92.2 | 0.30 |
| 16 | 40 | | mole % | 68.2 | 10.3 | 6.7 | 0.00 | 0.50 | 14.3 |

*MTD (metric ton per day);
†0.2 wt % higher alcohols

The invention claimed is:

1. Process for the preparation of methanol, comprising the steps of
   a) reacting carbon oxides and hydrogen in the presence of a methanol catalyst in a first methanol reactor to obtain a first methanol-containing effluent;
   b) introducing and reacting unconverted synthesis gas in a second methanol reactor in the presence of a methanol catalyst to obtain a second methanol-containing effluent, the first methanol reactor and the second methanol reactor being connected in parallel;
   c) combining the first and second effluent, and
   d) cooling and separating the combined and cooled effluent into a methanol-containing liquid phase and unconverted synthesis gas,
   wherein the first methanol reactor is a boiling-water reactor and the second methanol reactor is a gas-cooled reactor or a multistage packed-bed reactor.

2. The process of claim 1, wherein the methanol catalyst in the first methanol reactor is indirectly cooled by boiling water and the methanol catalyst in the second methanol reactor is indirectly cooled by the unconverted synthesis gas prior to conversion into the second effluent.

3. The process of claim 1, wherein the carbon oxides and hydrogen in the boiling-water reactor and the gas-cooled reactor are provided by a mixture of fresh synthesis gas and a part of the unconverted synthesis gas.

4. The process of claim 3, wherein the gaseous phase is contacted with the methanol catalyst after having directly or indirectly cooled the methanol catalyst in the second reactor.

5. The process of claim 1, wherein the carbon oxides and hydrogen in the boiling-water reactor are provided by a mixture of fresh synthesis gas and the gaseous phase from step d).

6. The process of 1, wherein the carbon oxides and hydrogen in the gas-cooled reactor are provided by a mixture of the gaseous phase from step d) and the fresh synthesis gas.

7. Process for the preparation of methanol, comprising the steps of
   a) reacting a methanol free feed gas comprising carbon oxides and hydrogen in the presence of a methanol catalyst in a first methanol reactor to obtain a first methanol-containing effluent;
   b) introducing and reacting unconverted synthesis gas in a second methanol reactor in the presence of a methanol catalyst to obtain a second methanol-containing effluent, the first methanol reactor and the second methanol reactor being connected in parallel;
   c) combining the first and second effluent, and
   d) cooling and separating the combined and cooled effluent into a methanol-containing liquid phase and unconverted synthesis gas,
   wherein the first methanol reactor is a boiling-water reactor and the second methanol reactor is a gas-cooled reactor or a multistage packed-bed reactor.

8. The process of 7, wherein separated and cooled synthesis gas is recycled to at least one of the first and second rectors.

* * * * *